US00PP23176P2

(12) United States Plant Patent
Suzuki

(10) Patent No.: US PP23,176 P2
(45) Date of Patent: Nov. 13, 2012

(54) ***LOROPETALUM* NAMED 'KUROBIJIN'**

(50) Latin Name: *Loropetalum chinense*
Varietal Denomination: Kurobijin

(76) Inventor: Yuji Suzuki, Kawaguchi (JP)

( * ) Notice: Subject to any disclaimer, the term of this patent is extended or adjusted under 35 U.S.C. 154(b) by 35 days.

(21) Appl. No.: 13/068,824

(22) Filed: May 20, 2011

(51) Int. Cl.
*A01H 5/00* (2006.01)

(52) U.S. Cl. ..... Plt./226

(58) Field of Classification Search ..... Plt./226
See application file for complete search history.

*Primary Examiner* — Susan McCormick Ewoldt
(74) *Attorney, Agent, or Firm* — Penny J. Aguirre

(57) ABSTRACT

A new and distinctive cultivar of *Loropetalum* named 'Kurobijin' that is characterized by its compact plant habit, its flowers that are deep red-purple in color, its late blooming period, its foliage that is dark burgundy in color with the color persisting throughout the summer, and its oval shaped leaves.

2 Drawing Sheets

Botanical classification: *Loropetalum chinense.*
Variety denomination: 'Kurobijin'.

BACKGROUND OF THE INVENTION

The present invention relates to a new and distinct cultivar of *Loropetalum chinense* and will be referred to hereafter by its cultivar name, 'Kurobijin'. 'Kurobijin' is a deciduous shrub grown for use as an ornamental landscape plant.

The Inventor discovered the new cultivar as a naturally occurring whole plant mutation (chance seedling) in a field plot at a nursery in Kawaguchi City, Japan in 1997. The parents of 'Kurobijin' are unknown.

Asexual reproduction of the new cultivar was first accomplished by the Inventor using softwood cuttings in Kawaguchi City, Japan in 2009. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Kurobijin' as a unique cultivar of *Loropetalum.*

1. 'Kurobijin' exhibits a compact plant habit, reaching a maximum of 2.5 feet in height and width.
2. 'Kurobijin' exhibits flowers that are deep red-purple in color.
3. 'Kurobijin' blooms 3 to 4 weeks later than is typical of cultivars of *Loropetalum* known to the Inventor.
4. 'Kurobijin' exhibits foliage that is dark burgundy in color with the color persisting throughout the summer.
5. 'Kurobijin' exhibits oval shaped leaves.

The new cultivar can be compared to the cultivars 'Hines Dark Leaf' (not patented), and 'Burgundy' (not patented). 'Hines Dark Leaf' is similar to 'Kurobijin' in having dark burgundy colored foliage, however, 'Hines Dark Leaf' differs from 'Kurobijin' in blooming 3 to 4 weeks earlier, in having lighter colored flowers, and in being taller in height (reaches up to 10 feet in height). 'Burgundy' is similar to 'Kurobijin' in having burgundy colored foliage, however, 'Burgundy' differs from 'Kurobijin' in having foliage that loses its burgundy color in summer, in blooming 3 to 4 weeks earlier, and in being taller in height (reaches up to 10 feet in height).

BRIEF DESCRIPTION OF THE DRAWING

The accompanying colored photographs illustrate the overall appearance and distinct characteristics of a the new *Loropetalum*. The photographs were taken of a three year-old plant as grown outdoors in a one-gallon container in Kawaguchi City, Japan.

The photograph in FIG. 1 is side view of a plant of 'Kurobijin' in summer.

Figure 1:
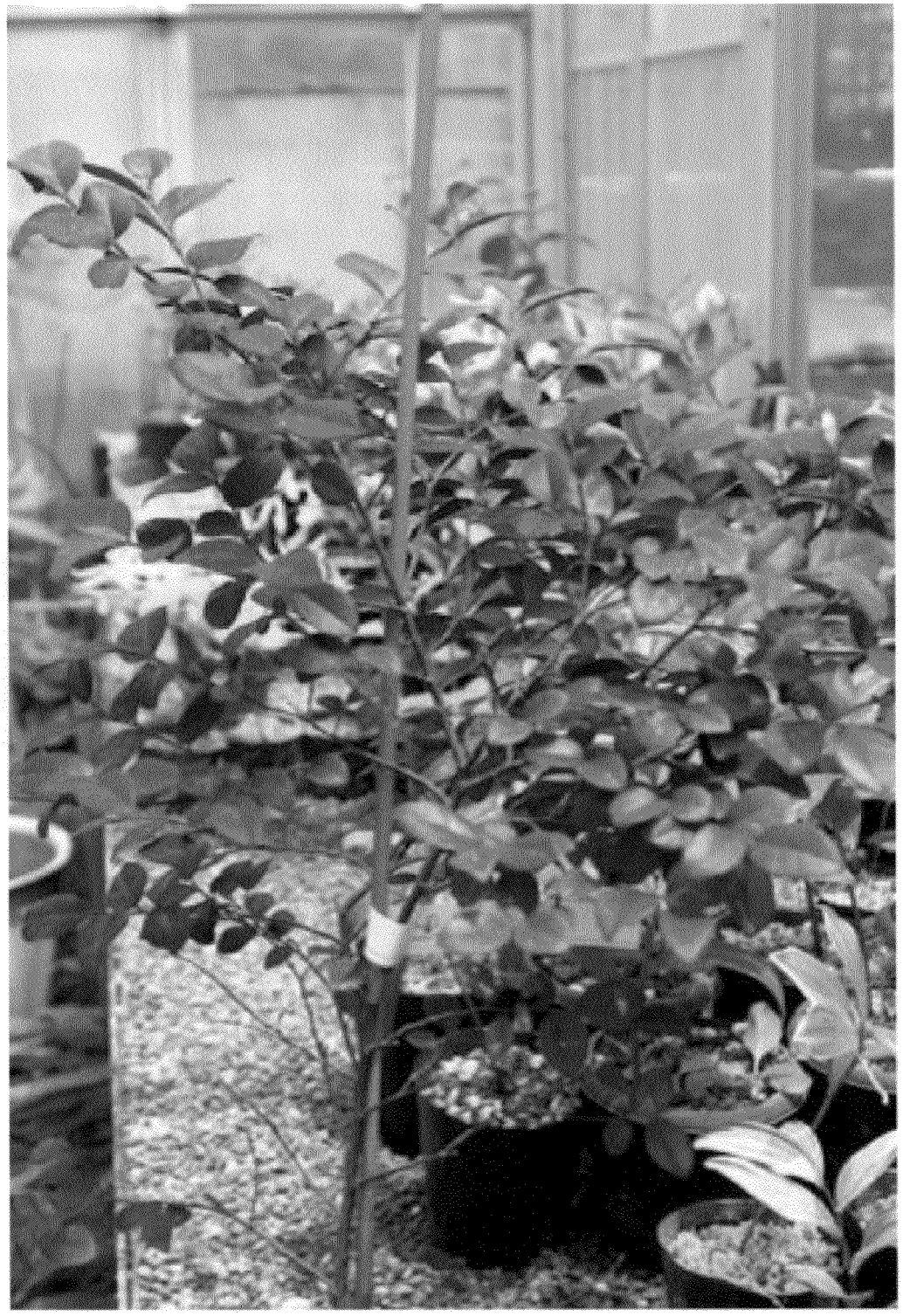
Figure 2:
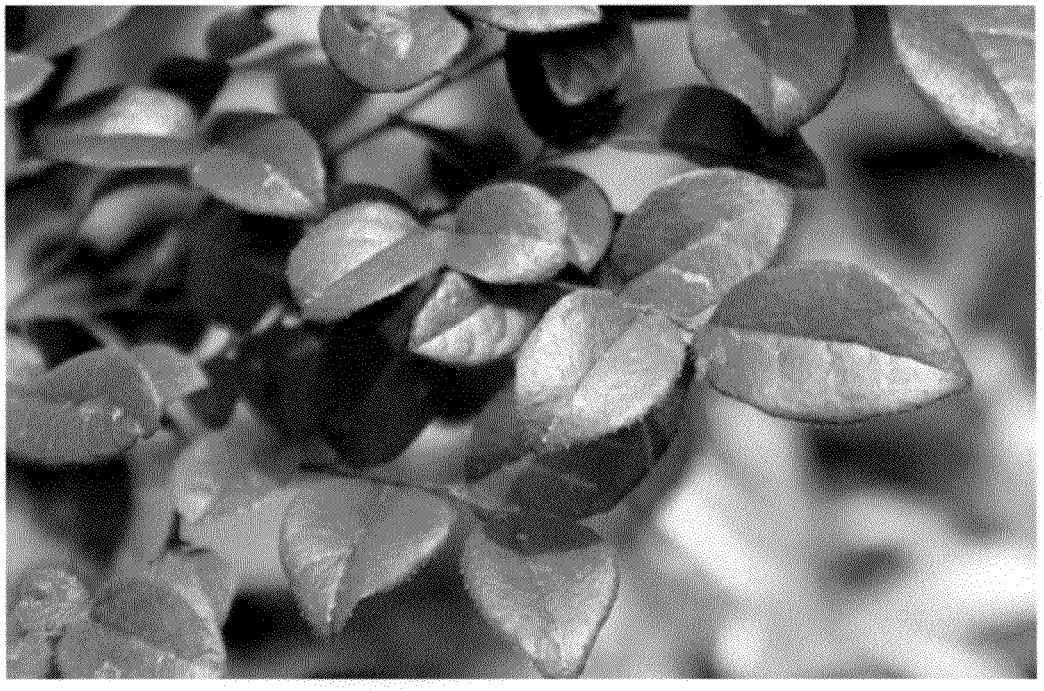

The photograph in FIG. 2 provides a close-up view of the foliage of 'Kurobijin'.

Figure 3:
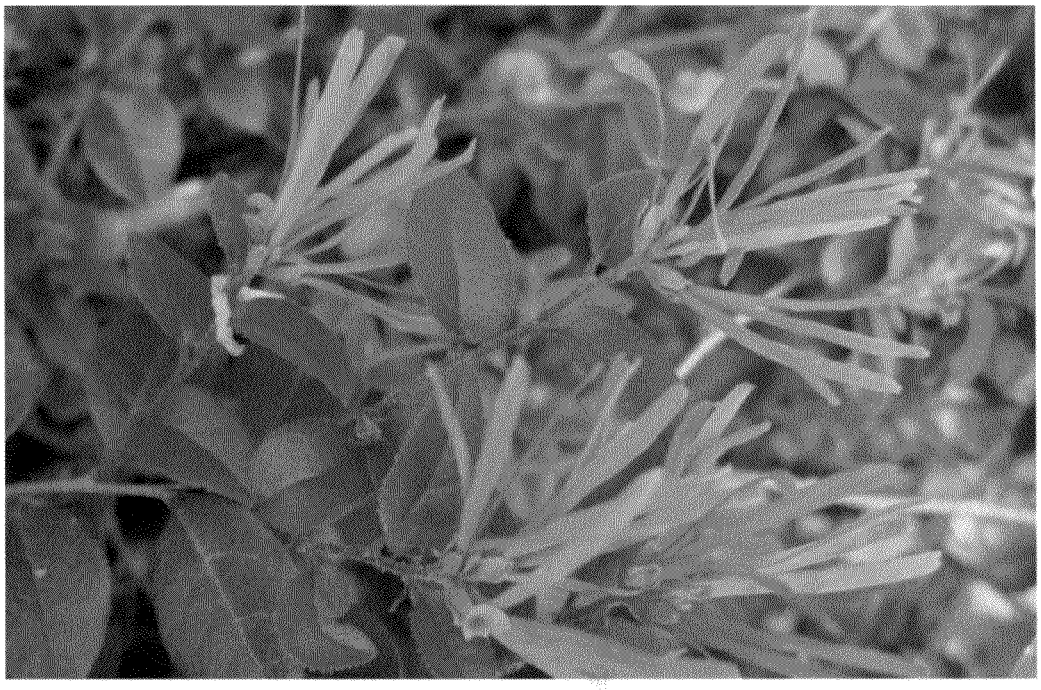

The photograph in FIG. 3 provides a close-up view of the inflorescences of 'Kurobijin'.

The colors in the photograph may differ slightly from the color values cited in the detailed botanical description, which accurately describe the colors of the new *Loropetalum.*

DETAILED BOTANICAL DESCRIPTION

The following is a detailed description of a fourteen year-old plant of the new *Loropetalum* as grown outdoors in a landscape in Kawaguchi City, Japan. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Plant description:

*Plant habit.*—Mounded, compact.

*Height and spread.*—Reaches about 76 cm (2.5 feet) in height and spread.

*Diseases and pests.*—No more susceptibility or resistance to pest or diseases than other *Loropetalums.*

*Hardiness.*—U.S.D.A. Zones 7 to 10.

*Branching habit.*—Densely branched, primarily alternate, emerge upright at an angle of 45° and cascade downward, lateral branches are an average of 70 cm in length and 1 cm in width becoming 1 mm or less in diameter at branch apex, numerous secondary lateral branches.

*Propagation*.—Vegetative softwood cuttings.

*Growth rate*.—Moderate.

Stem description:

*Branch color*.—N186A.

*Internode length*.—0.5 to 1.5 cm.

Leaf description:

*Leaf orientation*.—Outward, flattened to slightly reflexed.

*Leaf division*.—Simple.

*Leaf arrangement*.—Alternate.

*Leaf shape*.—Oval.

*Leaf size*.—1.5 to 2.5 cm in length, 1 to 1.5 cm in width.

*Leaf apex*.—Acute to obtuse.

*Leaf base*.—Obtuse to cuneate, occasionally asymmetrical.

*Leaf surface*.—Firm to leathery, upper surface glossy with impressed veins, lower surface glaucous.

*Leaf margin*.—Entire with stellate hairs.

*Leaf color*.—New growth upper surface; 187A, new growth lower surface; N79A, mature growth upper surface; N186A, mature growth lower surface; 187B.

*Leaf venation*.—Pinnate; new growth upper surface; 187A, new growth lower surface; N79A, mature upper surface; N186A, mature lower surface; 186A with scattered stellate hairs on midrib.

*Petioles*.—1 to 3 mm in length, 0.8 mm in width, color of upper and lower surfaces N186C.

Inflorescence description:

*Flowering period*.—Late April into early May, occasional repeat bloom throughout the growing season in Kawaguchi, Japan.

*Lastingness of blooms*.—2 to 3 weeks.

*Number of flowers*.—4 to 8 flowers per inflorescence.

*Inflorescence type*.—Terminal raceme, occasionally solitary at terminals or leaf axils.

*Inflorescence size*.—An average of 1.5 cm in length and 3 cm in width.

Flower description:

*Flower form*.—Perfect, strap-like.

*Flower buds*.—60A in color, average of 2 mm in length and 2 mm in diameter.

*Flower size*.—1.5 to 2.0 cm in length and 0.8 to 1.2 mm in width.

*Flower fragrance*.—None.

*Flower aspect*.—Outward.

*Petals*.—4, about 1.5 cm in length and 1 mm in width, linear in shape, apex and base truncate, entire margin, upper and lower surface smooth, ranges from 55B to 51A, 53C, 52A, and 53D in color.

*Sepals*.—4, about 3 mm in length and 1 mm in width, fused on lower half, upper and lower surface is smooth, color of upper and lower surface is 55B with lower half suffused with N186C.

*Pedicel*.—An average of 1 mm in length and 0.5 mm in width, pubescent surface, N186C in color.

*Peduncles*.—An average of 5 mm in length and 0.75 mm in width, pubescent surface, N186C in color.

Reproductive organs:

*Pistil*.—2, stigmas bifid, ovary 51B in color.

*Stamens*.—4 per flower, pollen sparse in quantity and about 155C in color.

*Fruit*.—2-horned capsule, ovoid in shape, an average of 5 mm in length and 6 mm in diameter, 75 to 100 per plant, skin is woody and N199B in color, 2 seeds per capsule.

It is claimed:

1. A new and distinct cultivar of *Loropetalum* plant named 'Kurobijin' as herein illustrated and described.

* * * * *